US009593309B2

(12) United States Patent
Coleman et al.

(10) Patent No.: US 9,593,309 B2
(45) Date of Patent: Mar. 14, 2017

(54) MEDIA FOR CULTURING, PRESERVING, AND ADMINISTERING REGENERATIVE CELLS

(71) Applicants:InGeneron, Inc., Houston, TX (US); ArthroDynamic Technologies, Animal Health Division, Inc., Lexington, KY (US)

(72) Inventors: Michael Coleman, Houston, TX (US); Ivone Bruno, Houston, TX (US); Rudy Martinez, Houston, TX (US); Amir Sanchez, Houston, TX (US); Eckhard Alt, Houston, TX (US); Frank D. Marcum, Lexington, KY (US); Paul Shealy, Savannah, GA (US)

(73) Assignees: ArthroDynamic Holdings, LLC, Lexington, KY (US); InGeneron Incorporated, Houston, TX (US)

( * ) Notice: Subject to any disclaimer, the term of this patent is extended or adjusted under 35 U.S.C. 154(b) by 0 days.

(21) Appl. No.: 14/707,564

(22) Filed: May 8, 2015

(65) Prior Publication Data

US 2015/0240211 A1 Aug. 27, 2015

Related U.S. Application Data

(63) Continuation of application No. PCT/US2013/069206, filed on Nov. 8, 2013.

(60) Provisional application No. 61/724,285, filed on Nov. 8, 2012.

(51) Int. Cl.
| *C12N 5/0775* | (2010.01) |
| *A01N 1/02* | (2006.01) |
| *C12N 5/00* | (2006.01) |
| *A61K 31/737* | (2006.01) |
| *A61K 35/28* | (2015.01) |

(52) U.S. Cl.
CPC ......... *C12N 5/0667* (2013.01); *A01N 1/0221* (2013.01); *A61K 31/737* (2013.01); *A61K 35/28* (2013.01); *C12N 5/0018* (2013.01); *C12N 2501/90* (2013.01); *C12N 2501/905* (2013.01); *C12N 2533/70* (2013.01); *C12N 2533/80* (2013.01)

(58) Field of Classification Search
None
See application file for complete search history.

(56) References Cited

U.S. PATENT DOCUMENTS

| 7,485,629 | B2 | 2/2009 | Marcum | |
| 2003/0216348 | A1 | 11/2003 | Henderson et al. | |
| 2004/0267362 | A1* | 12/2004 | Hwang | A61F 2/08 623/13.15 |
| 2006/0134781 | A1 | 6/2006 | Yang et al. | |
| 2007/0155009 | A1* | 7/2007 | McClelland | C12N 5/0672 435/325 |
| 2008/0248570 | A1 | 10/2008 | Turner et al. | |
| 2008/0318316 | A1 | 12/2008 | Reid et al. | |
| 2009/0148420 | A1* | 6/2009 | Cool | A61K 31/727 424/93.7 |
| 2012/0276173 | A1 | 11/2012 | Marcum et al. | |

FOREIGN PATENT DOCUMENTS

WO    2011/120535 A1    10/2011

OTHER PUBLICATIONS

Cho et al. "Application of porous glycosaminoglycan-based scaffolds for expansion of human cord blood stem cells in perfusion culture" Journal of Biomedical Materials Research Part A, vol. 86A, Issue 1, pp. 98-107, Jul. 2008.*
Wang "Heparan Sulfate Proteoglycan in Inflammation and Angiogenesis" Chapter 1 of Glycans in Diseases and Therapeutics, Edited by Mauro S.G. Pavao, 2011, 40 pgs.*
Kern et al. "Comparative Analysis of Mesenchymal Stem Cells from Bone Marrow, Umbilical Cord Blood, or Adipose Tissue" Stem Cells 2006;24: 1294-1301.*
PCT International Search Report for PCT Application No. PCT/US2013/069206 mailed Feb. 24, 2014 (4 pages).
Muzzarelli et al., "Chitosan, Hyaluronan and Chondroitin Sulfate in Tissue Engineering for Cartilage Regeneration: A Review," Carbohydrate Polymers, 2012, 89:723-739.
Supplementary European Search Report for EP Application No. 13853120 mailed May 4, 2016 (7 pages).

* cited by examiner

*Primary Examiner* — Thane Underdahl
(74) *Attorney, Agent, or Firm* — Sutherland Asbill & Brennan LLP

(57) ABSTRACT

A culture media, media supplement, or soluble matrix for cryopreservation or enhanced regenerative cell growth in culture and maintenance of multi-lineage differentiation potentiation. The inventive culture media, media supplement, or soluble matrix comprises a GAG composition comprising a sulfated GAG, such as chondroitin sulfate. A soluble matrix, a cell administration package or kit comprising the soluble matrix and a device for cell administration, and a method of use thereof, for administration of regenerative cells for treating a joint disease or other weakened or damaged tissue comprising the specified GAG compositions are further provided.

10 Claims, 15 Drawing Sheets

HA= Hyaluronic Acid
GAG= poly-sulfated Glycosaminoglycan
NAG= N-acetyl D-glucosamine
CS= Chondroitin Sulfate

| Cell Surface Marker | Single Color Cultured Cells Control (Po) | 8%DMS | 5%Po | 10%Po | 20%Po | 80%Po |
|---|---|---|---|---|---|---|
| CD34 | 35.84 | 42.88 | 58.18 | 58.03 | 58.2 | 52.17 |
| CD105 | 25.1 | 9.82 | 18.66 | 18.8 | 18.76 | 22.37 |
| CD90 | 55.36 | 62.34 | 74.41 | 73.96 | 73.41 | 69.46 |
| CD45 | 12.02 | -3.35 | -8.13 | -8.29 | -12.58 | -4.57 |
| CD146 | 30.19 | 14.73 | 19.58 | 19.56 | 27.19 | 28.54 |
| CD44 | 28.51 | 10.48 | -2.04 | 0.77 | -4.24 | 7.26 |
| CD117 | 25.72 | 6.28 | 1.56 | 4.52 | -1.69 | 7.81 |
| CD73 | 16.18 | 24.57 | 23.83 | 29.69 | 23.64 | 29.8 |

MEDIA FOR CULTURING, PRESERVING, AND ADMINISTERING REGENERATIVE CELLS

CROSS-REFERENCE TO RELATED APPLICATIONS

This application is a continuation of PCT Application No. PCT/US2013/069206 filed Nov. 8, 2013 which claims priority to U.S. Provisional Application No. 61/724,285 filed Nov. 8, 2012, the entire contents of which are hereby incorporated by reference.

FIELD OF THE INVENTION

The present invention is generally directed to compositions and methods for preserving, suspending, cryopreserving, or culturing cells, including regenerative stem cells, and uses for administration to repair or enhance weakened or damaged tissues, such as in joints, subcutaneous tissue, or organs, in animals and humans. More particularly, the present invention provides a media, media supplement, or soluble matrix, and method of use thereof, comprising a composition of glycosaminoglycans for preserving, suspending, cryopreserving, or culturing regenerative cells, enhancing regenerative cell growth in culture, and maintaining multi-lineage differentiation potential. The invention is also generally directed to therapeutic administration of such cells either isolated from the media or co-administered therewith.

BACKGROUND OF THE INVENTION

Glycosaminoglycans (GAGs) are important components of the extracellular matrix and play important regulatory roles in cell and tissue physiology and pathophysiology. GAGs are long unbranched polysaccharides consisting of a repeating disaccharide unit. The repeating unit consists of a hexose (six-carbon sugar) or a hexuronic acid, linked to a hexosamine (six-carbon sugar containing nitrogen). GAGs form an important component of connective tissues. GAG chains may be covalently linked to a protein to form proteoglycans. Proteoglycans and collagen are the chief structural elements of all connective tissues. Their synthesis is essential for proper maintenance and repair of connective tissues. In vitro, the introduction of glucosamine, a key precursor for GAGs, has been demonstrated to increase the synthesis of collagen and GAGs in fibroblasts. In vivo, topical application of glucosamine has enhanced wound healing. Glucosamine has also exhibited reproducible improvement in symptoms and cartilage integrity in humans with osteoarthritis (L. Bucci, Nutritional Supplement Advisor, July 1992).

The major proteoglycans found in connective tissue such as cartilage are chondroitin sulfate, dermatan sulfate, keratan sulfate and hyaluronic acid (also known as hyaluronan or HA). Heparin sulfate is also a proteoglycan, although it is not a component of articular cartilage. Newer names for proteoglycans sometime reference function of the core protein within the molecule found in chondroitin sulfate and keratin sulfate, e.g., aggrecan, a large proteoglycan that aggregates with hyaluronan, or reference location (e.g., decorin (dermatan sulfate), which decorates type I collagen fibrils), or reference primary structure, biglycan which has two glycoaminoglycan chains. Chondrocytes are active cells within the cartilage matrix, which manufacture new collagen and proteoglycan molecules while excreting enzymes, which aid in removal of damaged cartilage and proteoglycans. In other tissue with a high content of extracellular matrix such as tendons, ligaments, subcutaneous connective tissue or bone, tissue-specific cells provide the respective function of synthesizing the appropriate composition of extracellular matrix.

Hyaluronan is an integral part of both synovial fluid and articular cartilage, as exemplary tissues. Within the articular cartilage, hyaluronan provides viscoelastic properties allowing ease of motion between opposing surfaces and increasing compressive resistance. Within the synovium, hyaluronan, as a component of synovial fluid, provides an effective barrier regulating the introduction of plasma components. Under normal conditions, the body will synthesize sufficient amounts of base components to maintain and grow healthy articular cartilage, while limiting the production and release of destructive proteinases, inflammatory mediators and catabolic enzymes.

Hyaluronan or hyaluronic acid is a natural, highly charged, polyanionic molecule composed of alternating units of D-glucuronic and 2-acetamido-2-deoxy-D-glucose. These unbranched, coiled, elongated polysaccharide chains maintain a large negative electrostatic charge that attracts water molecules and allow the deformation of the molecular coil as ice crystallisation occurs during freezing and thawing. It is believed that hyaluronic acid coats and protects cells and tissues by attaching to the CD44 receptor sites on cells. Hyaluronic acid and other complex GAG formulations are frequently administered by intra-articular injection to treat joint disease, including osteoarthritis wherein they improve clinical symptoms and slow disease progression. Another example is the rebuilding of subcutaneous structures with the injection of hyaluronic acid or hyaluronic acid and other complex GAG formulations.

Chondroitin sulfate is broken down into sulfate disaccharides and N-acetyl galactosamine. Chondroitin sulfate, as CS4 and CS6 sulfated forms, within the body, is thought to be an essential glycosaminoglycan that binds water to the articular cartilage matrix and is necessary for the formation of proteoglycans. In particular, chondroitin sulfate is a long hydrophilic chain of repeating sugars. This glycosaminoglycan binds to proteoglycan molecules aiding in water and nutrient transportation within the articular cartilage. Chondroitin in its sulfate form includes galactosamine, a primary substrate of hyaluronan and a disaccharide pathway for proteoglycan synthesis secondary to the hexosamine pathways utilised for glycosaminoglycan production. Chondroitin sulfate chains comprise the space formation of the cartilage matrix and integral parts of the proteoglycan molecule. Chondroitin stimulates the production of proteoglycans, glycosaminoglycans, and collagen, which are the building blocks of healthy cartilage. Chondroitin sulfate also inhibits the secretion of degenerative enzymes by the chondrocytes within articular cartilage. Chondroitin sulfates are non-toxic and work synergistically with glucosamine to hydrate and repair articular cartilage.

Glucosamine is an amino sugar and a precursor for glycosaminoglycans (GAGs). Glucosamine, as glucosamine 5-phosphate, is naturally occurring within the body and is a component in the biosynthesis of glycosaminoglycans, proteoglycans, hyaluronan, and collagen. Glucosamine is available in exogenous forms, glucosamine sulfate sodium, glucosamine hydrochloride and N-acetyl D-glucosamine. N-acetyl D-glucosamine is also a derivative of glucose obtained by chemical hydrolysis of chitin. This polysaccharide is readily soluble in water and extremely bioavailable. N-acetyl D-glucosamine binds to glucuronic acid as well as galactose making it a precursor to hyaluronic acid, keratan-sulfate and chondroitin sulfate. This unique derivative aids in proteoglycan, collagen and glycosaminoglycan production. N-acetyl D-glucosamine has also been shown to aid in the healing of soft tissue injury. D-Glucuronic acid is a key substrate comprising one half of the hyaluronan molecule, the other being N-acetyl D-glucosamine.

Supplemental glucosamine has the ability to influence connective tissue such as cartilage, and so may apply to alleviation of various dysfunctions including arthritis. In the joint, for example, chondroitin sulfate acts to stimulate the production of proteoglycans, glycosaminoglycans, and collagen, inhibits degenerative enzymes excreted by the chondrocytes, and synoviocytes, and aids in nutrient transportation within the synovial fluid. Glucosamine, in particular N-acetyl D-glucosamine, increases the synoviocyte and chondrocyte production and subsequent availability of endogenous hyaluronan by the direct in situ inclusion of its prime substrates galactosamine (through chondroitin sulfate assimilation) and N-acetyl D-glucosamine. The exogenous hyaluronan acts to replace depleted endogenous hyaluronan and to lubricate and coat healthy as well as damaged articular tissue during the reparative process.

A GAG composition marketed as a veterinary medical device as POLYGLYCAN (ArthroDynamic Technologies) comprises chondroitin sulfate, N-acetyl D-glucosamine, and hyaluronic acid. Such proteoglycan compositions are described in U.S. Pat. Nos. 6,979,679 and 7,485,629, which are hereby incorporated by reference in their entireties.

Regenerative cells found in multi-cellular organisms are cells capable of promoting tissue repair and regeneration and reducing inflammation. Stem cells are regenerative cells that can differentiate into a diverse range of specialized cell types. The two broad types of mammalian stem cells are: embryonic stem cells that are found in blastocysts, and adult stem cells that are found in adult tissues. The two classical properties of stem cells are self-renewal and potency. Self-renewal refers to the ability to go through numerous cycles of cell division while maintaining the undifferentiated state, and potency refers to the capacity to differentiate into specialized cell types. Potency specifies the differentiation potential of the stem cells to differentiate into different cell types. For instance, totipotent stem cells are cells produced from the fusion of an egg and sperm cell, as well as the first few divisions of the fertilised egg, they can differentiate into embryonic and extra-embryonic cell types. Pluripotent stem cells are the descendants of totipotent cells and can differentiate into cells derived from any of the three germ layers. Multipotent stem cells can produce only cells of a closely related family of cells (e.g. hematopoietic stem cells differentiate into red blood cells, white blood cells, platelets, etc.). Unipotent cells can produce only one cell type, but have the property of self-renewal that distinguishes them from non-stem cells (e.g., muscle stem cells). In addition, a regenerative cell population frequently comprises not only cells but also microsomes released by the regenerative cells that are important in functions such as immunomodulation inside the body.

Progenitor cells refer to immature or partially undifferentiated regenerative cells, typically found in post-natal animals. Like stem cells, progenitor cells have a capacity for self-renewal and differentiation, although these properties may be more limited. Embryonic stem cells are pluripotent and show unlimited capacity for self-renewal. Thus, they are sometimes referred to as true stem cells. In contrast, many cells termed adult stem cells would be better defined as progenitor cells, as their capacities for unlimited self renewal and plasticity have not been comprehensively demonstrated. The majority of progenitor cells are dormant or exhibit little activity in the tissue in which they reside. They exhibit slow growth and their main role is to replace cells lost by normal attrition. However, upon tissue damage or injury, progenitor cells can be activated by growth factors or cytokines, leading to increased cell division important for the repair process. Examples of progenitor cells include satellite cells found in muscle and the transit-amplifying neural progenitors of the rostral migratory stream.

Mesenchymal stem cells ("MSCs") (i.e., stromal cells) are pluripotent regenerative cells that can differentiate into a variety of cell types. MSCs can be derived from many tissues including bone marrow, adipose, umbilical cord, and dental pulp. MSCs adhere to plastic tissue culture and are commonly selected from more diverse regerative cell populations based on this property of plastic adherence. For example, bone marrow MSCs (BM-MSCs) can be selected from the cell population present in a bone marrow aspirate by culturing the cells that adhere to the plastic tissue culture surface, and adipose MSC (Ad-MSC) can be selected from adipose stromal vascular fraction (SVF) cells in the same manner. Adipose SVF is the non lipid-filled cell population from adipose tissue and contains a high proportion of regenerative cells. Among the cell types that MSCs have been shown to differentiate into in vitro or in vivo are osteoblasts, chondrocytes, myocytes, adipocytes, neuronal cells, and beta-pancreatic islets cells. MSCs provide the supportive structure in which the functional cells of the tissue reside. In addition, MSCs play roles in tissue healing and repair.

Because in adult organisms, MSCs act as a repair system for the body replenishing specialized cells but also maintaining tissue homeostasis and they are capable of differentiating into different types of tissues, they have been utilized in the treatment of, for example, skeletal and connective tissue disorders.

There is increasing evidence that regenerative cells derived from other tissue, such as adipose-derived regenerative cells, are equally or even more capable than bone marrow derived regenerative cells in repairing or alleviating connective tissue dysfunctions. (See, Toghraie et al., "Treatment of Osteoarthritis with Infra-Patellar Fat Pad Derived Mesenchymal Stem Cells in Rabbit," Knee, 2011, 18(2):71-75; and Frisbie et al., "Evaluation of Adipose Derived Stromal Vascular Fraction or Bone Marrow Derived Mesenchymal Stem Cells for Treatment of Osteoarthritis," J. Orthop. Res., 2009, 27(12):1675-1680.)

Intra-articular administration of stem and regenerative cells, particularly MSCs from adipose tissue and bone marrow, is increasingly utilized in clinical practice. Current practice is to administer cells suspended in an inactive carrier such as saline or platelet rich plasma, or in a single component non-sulfated GAG, such as hyaluronan. To date, minimal data have been reported as to the effects of GAGs on stem and regenerative cells and on the optimal composition of GAG formulations for combination with stem and regenerative cells for in vitro and in vivo applications.

SUMMARY OF THE INVENTION

Use of cells suspended in a GAG composition that includes hyaluronic acid in combination with at least one sulfated GAG, either as an acceptable admixture or in concurrent or sequential administration, is one aspect of the present invention. Administration of cells in such a GAG formulation provides benefits not only for intra-articular injection but also for other modes of administration such as subdermal, subcutaneous, topical, intra-muscular, intravenous, intra-capillary such as the cavernous body, intra-arterial, intra-thecal, directly into organs, into the urinary bladder, into tendons and the peri-tendineum, in the periosteum, and into cavities such as bone cysts.

In addition, culturing, preserving, or cryopreserving of cells in such a GAG composition provides benefits for cell proliferation, viability, and regenerative potential. The invention provides compositions and methods for the use of a GAG formulation that includes hyaluronic acid in combination with at least one sulfated GAG for culturing, suspending, preserving, cryopreserving, or administering or any combination thereof of cells derived from animals or humans.

In one aspect, the present invention provides a media supplement for enhanced effectiveness in preservation, suspension, storage, cryopreservation, culturing, growing, and proliferating cells, such as adipose-derived regenerative cells (ADRCs), while maintaining differentiation potential in vitro and in vivo. In certain embodiments, the media or media supplement of the present invention comprises a glycosaminoglycan (GAG) formulation comprising one or more GAGs in a defined concentration. In certain embodiments, particularly adapted for culturing, growing, and proliferating cells, while maintaining pluripotency, the specified GAG composition is diluted to a concentration of 1-10% (v/v), 2.5-7.5% (v/v), 3-7% (v/v), or 5% (v/v) based on the final volume of the media. In other embodiments, particularly adapted for preservation, suspension, storage and cryopreservation, the specified GAG formulation is diluted to a concentration of 5% (v/v), 10% (v/v), 20% (v/v), 30% (v/v), 40% (v/v), 50% (v/v), 60% (v/v), or 70% (v/v), or more based on the total volume of the media.

In an embodiment of the present invention, a media or media supplement comprising a GAG composition comprises proportions of about 1:20:20 (mg/ml) of hyaluronic acid (HA):chondroitin sulfate (CS):N-acetyl D-glucosamine (NaDg). Such a composition can, for example, comprise hyaluronic acid sodium salt (5 mg/ml), sodium chondroitin sulfate (100 mg/ml) (either or both CS4 and CS6 forms), and N-acetyl D-glucosamine (100 mg/ml) such as in the commercially available POLYGLYCAN composition. The proportions of the GAG composition of the present invention can also vary from 0.1-10 HA: 2-200 CS: 2-200 NaDg (mg/ml).

In certain embodiments, the present invention provides that adipose derived regenerative cells (ADRCs) proliferate more adherent cells, and are blocked from chondrogenic and osteogenic differentiation in the presence of a GAG combination of hyaluronic acid, chondroitin sulfate and N-acetyl D-glucosamine in the cell media at 1%-10% (v/v) or about 5% (v/v) concentration. In other embodiments, the present invention provides that a formulation containing only hyaluronic acid (HA) is pro-mitotic, but to a lesser magnitude.

One aspect of the present invention provides a method of enhancing an in vitro expansion rate of cells while maintaining differentiation potential. In this aspect, the invention method comprises culturing the cells in the culture media of the present invention, or treating the cells with the media supplement of the present invention, or coating the surface on which the cells are growing with a soluble matrix of the present invention, wherein the culture media, media supplement, cryopreservant, or soluble matrix of the present invention comprises a specified GAG composition, which comprises one or more GAGs at a defined concentration. In certain embodiments, the specified GAG formulation comprises a POLYGLYCAN composition of hyaluronic acid, chondroitin sulfate and N-acetyl D-glucosamine at a concentration of up to 50% (v/v), 1-10% (v/v), 3-7% (v/v), or about 5% (v/v). In other embodiments, the specified GAG formulation comprises hyaluronic acid (HA), and optionally a sulfated chondroitin, at a concentration of up to 50% (v/v), 1-10% (v/v), 2.5-7.5% (v/v) or 5% (v/v). In certain embodiments, the cells are cultured in such culture media of the present invention for hours and days, in some cases for 12-20 hours, before being harvested for further use. In other embodiments, the cultured cells remain in the media, or are exposed to supplemental media, before further use.

An aspect of the present invention further provides a soluble matrix comprising a specified GAG formulation for administration of cells for the treatment of diseases such as joint or other connective tissue damage. In certain embodiments, the specified GAG formulation in the soluble matrix comprises a POLYGLYCAN composition at a concentration of 1-20% (v/v). In other embodiments, the specified GAG formulation in the soluble matrix comprising hyaluronic acid, chondroitin sulfate, or other GAGs in the same ratio as those in the POLYGLYCAN composition. A cell administration package comprising the soluble matrix of an aspect of the present invention and a device for cell administration is also provided.

An aspect of the present invention further provides a method, and composition thereof, for preventing and treating a joint disease or other tissue damage, or specifically in the repair of cartilage and connective tissue, in an affected site in animals or humans by administering the cells cultured and proliferated in the culture media, or treated, stored or cryopreserved in the media or with the media supplement of the present invention. In certain embodiments, the cells are mixed with the soluble matrix of an aspect of the present invention comprising a specified GAG formulation, such as the POLYGLYCAN composition, for administration of the cells. The pharmaceutical preparation described herein comprises a POLYGLYCAN and other proteoglycan or GAG compositions in combination with cells. Methods of treatment are provided herein using the POLYGLYCAN composition and other proteoglycan or GAG compositions in combination with regenerative cells, either as a pharmaceutically acceptable admixture or in concurrent or sequential administration. A cell administration package or kit comprising the soluble matrix comprising a specified GAG formulation, and a device for cell administration are also provided.

DETAILED DESCRIPTION OF THE INVENTION

Figure 1A:
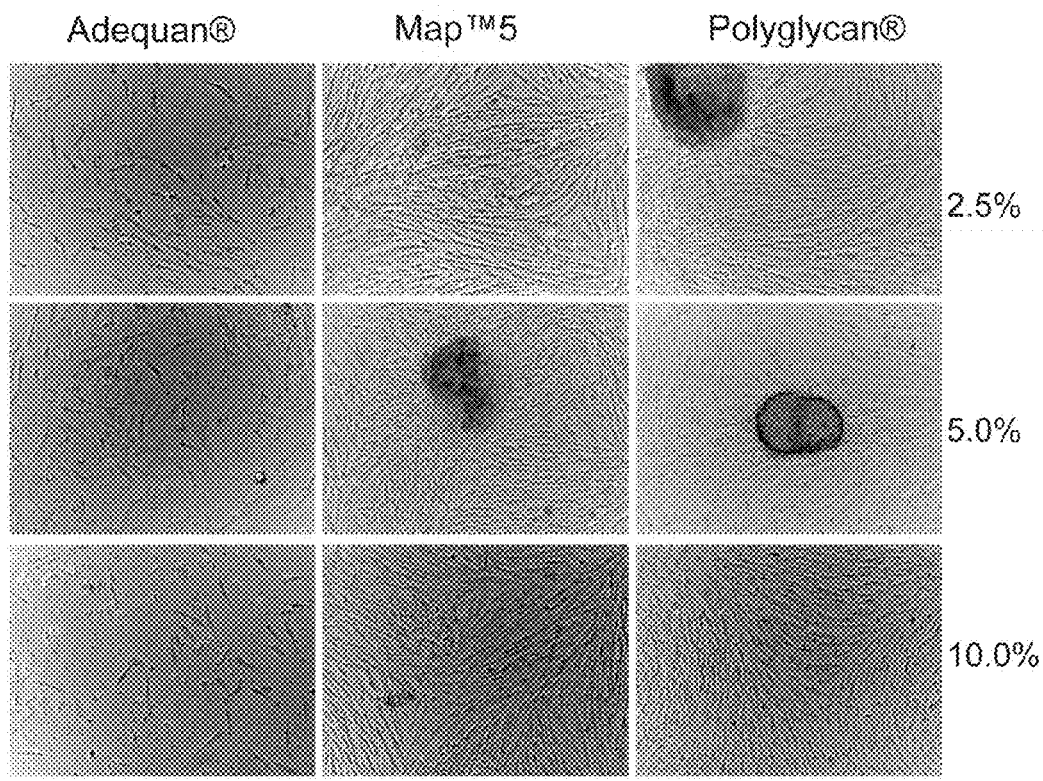
FIGS. 1A and 1B describe an effect of GAG concentration on proliferation on Ad-MSCs. Fresh canine adipose SVF cells were plated at equal nucleated cell density and grown for 7 days in culture on plastic tissue culture surface in the presence of complete growth media (α-MEM with 20% (v/v) FBS) and the respective concentrations (v/v) of GAG formulation (FIG. 1A). Nucleated cell counts were performed by Syto13 staining followed by hemacytometer counting under fluorescence microscopy (FIG. 1B).

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

In one aspect, the present invention provides a media or media supplement for enhanced cell growth and maintenance of differentiation potential. In one embodiment, the invention media or media supplement comprises a specified proteoglycan or GAG formulation, in certain embodiments comprising a POLYGLYCAN composition, or hyaluronic acid (HA) and other GAGs in a defined concentration. In certain embodiments, the invention media or media supplement comprises the POLYGLYCAN composition consisting of hyaluronic acid sodium salt (5 mg/ml), sodium chondroitin sulfate (100 mg/ml), and N-acetyl D-glucosamine (100 mg/ml). In certain embodiments, the media or media supplement comprises a composition in mg/ml proportions of about 1:20:20 of hyaluronic acid:chondroitin sulfate:N-acetyl D-glucosamine. Supplement compositions can comprise sodium hyaluronic acid and other sulfated glycosaminoglycans (GAGs). In another embodiment of the present invention, a media or media supplement comprising a composition in mg/ml proportions of about 1:10:10 of hyaluronic acid:chondroitin sulfate:N-acetyl D-glucosamine can be applied. As can be appreciated, the final dilution of the composition can be adjusted according to the intended use.

As used herein, the terms "proteoglycan composition" or "GAG formulation" or "GAG composition" described herein are used interchangeably, which refer to a composition or formulation comprising one or more glycosaminoglycans (GAGs), including but not limited to, hyaluronic acid, chondroitin sulfate and N-acetyl D-glucosamine, and is formulated into any acceptable formulations suitable for storage, cryopreservation, culture media, media supplement, or matrix, or for therapeutic administration. The GAG composition of the present invention includes, but is not limited to, a sterile solution or suspension, or matrix or gel that can be mixed with cells, or any cell culture, cryopreservation, or suspension media or media supplement, known or later developed in the art in culturing, administering, suspending, or cryopreserving regenerative cells, or can be used to coat the surface on which the regenerative cells are growing in any suitable media known or later developed in the art. Methods of treatment are provided herein using the GAG composition in combination with regenerative cells, either as an acceptable admixture or in concurrent or sequential administration. The GAG composition of the present invention can also be formulated for direct application or intra-articular, intramuscular, intravenous, subcutaneous, or other parenteral or systemic administration to a subject in need for treating a joint or other connective tissue damage or weakness, along with the regenerative cells.

Depending on the embodiments, various GAGs can be included in the specified GAG composition described herein. In certain embodiments, the GAG composition comprises, or consists essentially of, chondroitin sulfate, glucosamine, and hyaluronan. In certain embodiments, the GAG composition comprises, or consists essentially of, glucosamine and hyaluronan. In certain embodiments, the GAG composition comprises a mixture of chondroitin sulfate, poly-sulfated GAGs, glucosamine and hyaluronan, and can be stored in a single container at room temperature, in a refrigerator or a freezer. In other embodiments, the glucosamine, such as N-acetyl D-glucosamine, is stored in a separate container at room temperature, in a refrigerator or freezer, and can be mixed with the chondroitin sulfate and hyaluronan mixture before administration. In yet other embodiments, the GAG composition comprises chondroitin sulfate, (both CS4 and CS6 forms) hyaluronan, and glucosamine, such as N-acetyl D-glucosamine, all mixed together and stored in a single container ready for mixing with media, or coating the surface for cells to grow, or direct co-administration with the cells to a subject in need.

In certain embodiments, the GAG composition is the POLYGLYCAN composition (Arthrodynamic Technologies, Lexington, Ky.) consisting essentially of an effective amount of chondroitin sulfate, N-acetyl D-glucosamine, and hyaluronan (hyaluronic acid). In certain embodiments, the chondroitin sulfate in the proteoglycan composition is preferably chondroitin 4-sulfate (CS4), chondroitin 6-sulfate (CS6), or a mixture of both CS4 and CS6. An effective amount of chondroitin sulfate and N-acetyl D-glucosamine is preferably from between about 0.5 grams to about 1.5 grams of per unit dose, respectively, and an effective amount of hyaluronan is preferably from about 10 mg to about 50 mg per unit dose. The detailed descriptions of POLYGLYCAN composition, or its equivalents, and method of preparation and use of such composition are described in U.S. Pat. Nos. 6,979,679 and 7,485,629, and the entire contents of these patents are incorporated by reference herewith.

As used herein, the term "stem cells" or "regenerative cells" are used interchangeably and are cells capable of retaining the ability to reinvigorate themselves through mitotic cell division and which can differentiate into more than one specialized cell types. In one embodiment, the regenerative cells described herein are mesenchyme and/or stromal cells including, but not limited to, osteoblasts, chondrocytes, chondrocyte progenitor cells including mesenchymal stem cells or MSCs, fibroblasts, fibroblast-like cells, and SVF cells or other stromal cells capable of producing collagen types and proteoglycans which are typically produced in cartilaginous tissues. In yet another embodiment, the regenerative cells described herein are stromal cells capable of producing osteoblasts, adipocytes, and chondroblasts. In yet another embodiment, the regenerative cells described are able to differentiate into mesodermal, endodermal, or ectodermal lineages.

In yet another embodiment, the regenerative cells are chondrogenic stem and/or progenitor cells including mesenchymal stem cells or MCSs. In further embodiments, the mesenchymal stem cells or MCSs are animal mesenchymal stem cells isolated from an animal tissue specimen. In yet other embodiments, the progenitor cells can be obtained from a patient in an autologous or allogenic manner. The progenitor cells, fibroblast-like cells and other cells and/or elements that comprise the stroma may be fetal or adult in origin, and may be derived from convenient sources such as adipose, cartilage, bone, skin, ligaments, tendons, muscles, placenta, umbilical cord, etc. For example, stromal cells such as chondrocytes may be derived from any type of cartilage, including but not limited to, hyaline cartilage, costal cartilage, fibrous cartilage, etc., which can be obtained by biopsy (where appropriate) or upon autopsy.

Regenerative cells are typically used in the present invention in an isolated state, in that they are provided in concentrated numbers or a cellular culture free from at least some of the other constituents with which they are found in nature. Regenerative cells may be derived from various sources including adipose tissue, bone marrow, umbilical cord, placenta, dental pulp, tendons, muscle, or skin. Regenerative cells from a variety of sources may be used in the present invention.

The regenerative cells used in the present invention may be readily isolated by disaggregating an appropriate tissue. Furthermore, once cells have been isolated, their population can be expanded mitotically, and if preferred, enriched in certain cell types, in order to obtain the cell preparation for the combination with the glycosaminoglycans in the composition disclosed in the present invention.

In certain embodiments, the present invention provides that regenerative cell viability and proliferation of colony forming cells is enhanced while differentiation potential is preserved. In certain embodiments, the present invention facilitates plastic adherence of stromal cells and reduces anoikis-induced apoptosis.

In certain embodiments, the regenerative cells are preserved with one or more appropriate well-known additional cryoprotectants in the compositions described herein. In one embodiment, the regenerative cells provided herein, either uncultured or cultured, or previously preserved in the presence of one or more suitable cryoprotectants, can be combined with the compositions described herein. In addition, regenerative cells can be properly protected during the cryopreservation process when combined with the compositions described herein, yielding improved viability.

In certain embodiments, the effectiveness of the present invention is demonstrated by viable cell count and flow cytometry analysis of canine and human adipose SVF cells cryopreserved in various formulations containing different GAGs at different concentrations.

The present invention further provides a method, and composition thereof, for administering into a human or animal body regenerative cells cultured and proliferated in the culture media or treated with the media supplement or grown on the surface coated with the media supplement or matrix of the present invention. In certain embodiments, the regenerative cells are cultured, preserved, or cryopreserved in the media or media supplement of the present invention and then mixed with the matrix of the present invention comprising a specified GAG formulation, such as the POLYGLYCAN composition, or any other suitable GAG formulations, for administration of the regenerative cells. The preparation described herein comprises a POLYGLYCAN or any other GAG formulations in combination with regenerative cells. Methods of treatment are provided herein using the POLYGLYCAN or any other GAG formulation in combination with regenerative cells, either as an acceptable admixture or in concurrent or sequential administration. However, the dilution of the POLYGLYCAN or any other GAG formulation used in culturing, preservation, and cryopreservation may differ from the dilution used for the administration of regenerative cells. Dilution of GAG formulations used for administration of regenerative cells may vary depending on specifics of the condition of the patient and the anatomical site of administration.

As used herein, the preparation of the present invention is formulated in a suitable form, including, but not limited to, a form of sterile solution, suspension, a scaffold such as a stent, sponge, suture, or matrix, or a gel- or paste-like formulation. Molecular weights of the GAG in the GAG formulation can be selected to determine the physical properties of the suitable form. Administration of regenerative cells in such a GAG formulation provides benefits not only for intra-articular injection but also for other modes of administration such as subdermal, subcutaneous, topical, intra-muscular, intravenous, intra-capillary such as the cavernous body, intra-arterial, intra-thecal, directly into organs, into the urinary bladder, into tendons and the peritendineum, in the periosteum, and into cavities such as bone cysts. Systemic administrations can include, but are not limited to, intramuscular, intravenous or subcutaneous injection or via direct adsorption into the bloodstream via non-gastrointestinal transmucosal, e.g., sublingual administration.

It is contemplated by certain embodiments of the invention that the trasnsmucosal delivery can include any mucosal tissue that provides a mucosal surface area for direct adsorption into the blood stream and that does not subject the compositions of the invention to digestion and/or other alteration via gastric or intestinal enzymes. The compositions can be provided as liquids or semi-solids for direct application to the desired mucosal tissue. The compositions can be formulated into any of a variety of presentations designed to enhance and/or prolong contact with the desired mucosal tissue to promote adsorption into the bloodstream. For example, the compositions can be incorporated into a dissolvable or biodegradable film for placement e.g., under the tongue or as an oral or nasal spray or other presentation designed to enhance and/or prolong contact with the mucosa of the oropharnyx or other target tissue.

In yet another preferred embodiment, the compositions provided herewith are attached to a sheet of material adapted for implantation onto or between tissues of a human or animal body. Preferably, the compositions are impregnated into a polymeric gauze-like material or coated onto a gauze-like material or joined to the material by adhesion and/or capillary action. The material onto which the composition is attached may be either a permanent implant or it may be biodegradable. In yet another preferred embodiment, the composition provided herewith is attached to a bandage or other surgical materials, including, but not limited to, surgical suture material, surgical staple, or a device such as a buckle.

The pharmaceutical preparation described herein further may optionally comprise one or more other therapeutic agents, including, but not limited to, synthetic and non-synthetic corticosteroid agents, nonsteroidal anti-inflammatory drugs, analgesics, antirheumatics, immunoregulators, immunosuppressant, articular function augmenters, interleukin production inhibitors, or growth factor, all of which have therapeutic effects. Any drugs, agents, compounds, known and/or to be developed, showing any desired therapeutic effects are within the scope of this invention. In other embodiments, the invention may specifically exclude one or more of the above therapeutic agents. In yet another embodiment, the stem cells, or the pharmaceutically acceptable formulation comprising the regenerative cells, may further comprise other cells that aid in the production of one or more tissues including, for example, muscle, cardiac, neural, and connective tissues.

The composition of the present invention can be used in the prevention or treatment of connective tissue damage, which includes any primary or secondary diseases or injuries to the connective tissues in humans or animals. Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage.

Having discussed the media or media supplement comprising a specified GAG formulation, and the method of use thereof, providing an enhanced effectiveness of culturing, growing, preserving, cryopreserving, administering, and proliferating regenerative cells, while maintaining differentiation potentials, and for the treatment of animals and humans. It will be more clearly perceived and better understood from the following specific examples that are intended to provide examples of certain preferred embodiments and not limit the scope of the present invention.

EXAMPLES

Materials

POLYGLYCAN is a commercially available patented formulation of hyaluronic acid, sodium chondroitin sulfate and N-acetyl D-glucosamine used for post-surgical lavage of synovial compartments because it contains naturally occurring components of synovia that play a central role in maintaining the homeostatic environment of the joint. POLYGLYCAN is also designed to replace synovial fluid lost during surgery. Commercially available POLYGLYCAN (Arthrodynamic Technologies) is a highly viscous aqueous solution of defined fractions of purified hyaluronic acid, chondroitin sulfates C4 & C6 in a 10% solution of N-acetyl D-glucosamine. Each 10 mL vial contains 50.0 mg hyaluronic acid sodium salt, 1000 mg sodium chondroitin sulfate, and 1000 mg N-acetyl D-glucosamine.

Hyaluronic acid is a natural, highly charged, polyanionic molecule composed of alternating units of D-glucuronic and 2-acetamido-2-deoxy-D-glucose. These unbranched, coiled, elongated polysaccharide chains maintain a large negative electrostatic charge that attracts water molecules and allow the deformation of the molecular coil as ice crystallisation occurs during freezing and thawing. One commercially available source of hyaluronic acid is MAPS (Bioniche). ADEQUAN Canine (Luitpold Animal Health) is a prescription, water-based, intramuscular, polysulfated glycosaminoglycan (PSGAG).

Methods:

Adipose SVF cells were obtained from canine adipose tissue taken at spay procedures and from human lipoaspirate samples procured under IRB protocol and with informed consent from patients undergoing elective lipoplasty. Primary cell preparations were obtained using a point-of-care tissue processing system and associated disposables and reagent (ARC™ System and MATRASE™ Reagent, InGeneron, Inc. Houston, Tex.). Ad-MSC were obtained by culture of primary cells in Alpha DMEM, 20% (v/v) FBS, with antibiotic (pen/strep). Commercially available formulations of polysulfated glycosaminoglycans (ADEQUAN, Luitpold Animal Health, Shirley, N.Y.), a formulation of hyaluronic acid, N-acetyl D-glucosamine, and chondroitin sulfate (POLYGLYCAN, Arthrodynamic Technologies, Lexington, Ky.), and a formulation of hyaluronic acid (HA) (MAP-5, Bioniche, Athens, Ga.), and individual GAGs were tested at concentrations up to 50% (v/v).

Assays for cell proliferation, colony forming units (CFU), gene expression analyses, cell surface markers, and chondrogenic and osteogenic differentiation were performed.

Cell growth and Colony Forming Units (CFU) were grown in monolayer on tissue culture grade plastic in alpha MEM, 20% FBS (v/v), pen/strep. Nucleated cell counts were performed by staining with Syto13 (Invitrogen) followed by hemacytometer counting under fluorescence microscopy. Gene expression analysis was performed by quantitative RT-PCR profiling, BioRad iQ. Flow Activated Cell Storing (FACS) analyses were performed at M.D. Anderson Cancer Center FACS Core Facilities, Houston, Tex. by GALLIOS Flow Cytometry Instruments (Beckman Coulter). For osteogenic and chondrogenic differentiation, cells were cultured in STEMPRO induction media (Invitrogen, Carlsbad, Calif.) for 14 days, fixed in 4% formalin, and stained with Alzarin red and Alcian Blue, respectively. Statistical analyses were performed by ANOVA.

The SVF cells are obtained from subcutaneous adipose tissue by known methods, preferably by processing with the help of collagenase 1, collagenase 2, and the neutral protease in the MATRASE™ Reagent formulation. The typical cell count obtainable is between 600,000 and 1 million nucleated cells per gram of human subcutaneous adipose tissue, 1 million to 1.5 million per gram of, and 1.2 to 3 million per gram of equine adipose tissue. A higher number of cells can be obtained in those with a lower body mass index. This indicates that the relative percentage of adipose cells compared to the stromal vascular fraction is lower. Also, meaning that 1 gram of tissue contains relatively more interstitial stromal vascular component compared to the adipocytes, while in obese individuals the number of cells obtained per gram tissue is lower due to the higher relative percentage of adipocytes.

After recovering the cells, they were subjected to a 50% POLYGLYCAN dilution with serum (preferably autologous) and frozen by known methods whereby the temperature gradient by minute change was controlled in order to prevent cell rupture. The 50% POLYGLYCAN dilution—due to its composition and physical properties—prevented cell death. After storing in −18 degrees Celsius to −20 degrees Celsius, the rate of apoptosis after thawing compared to the rate of apoptosis at time of freezing was negligible. For prolong periods of preservation such as months and years, storage at −70 degrees Celsius or even lower degrees centigrade prevents cell death.

After thawing, the cells can be used for injection. However, if they are injected into a defined compartment such as a joint, a dilution at the final site of up to a 5 percent content of POLYGLYCAN may be beneficial. Such a dilution can be obtained by diluting the initial solution with regenerative cells from 50% to, for example, 10%. As an example: if the cells were frozen in 50% POLYGLYCAN in a glass vial of 1.8 ml, a further dilution to 9 ml would yield a 10% POLYGLYCAN content in which the regenerative cells are dispersed. Upon injection into, for example, a knee that typically has about 18 ml of synovial fluid, 9 ml of this synovial fluid is removed by puncture and 9 ml of regenerative cells solution will be injected making the final solution of the POLYGLYCAN in the knee joint a 5% solution which has shown a beneficial effect on cell growth.

Shipping of regenerative cells typically results in an increased rate of apoptosis even if the cells are kept in optimal culture conditions with temperature, media, and $CO_2$ adjusted to optimum levels. This is due to anoikis, which results from a lack of adherence to extracellular matrix. The GAG formulation of the present invention binds to certain cell surface receptors, such as the CD44 receptor and provides a natural matrix for preventing anoikis and is, therefore, in a formulation, such as that of the present invention, represents a preferable shipping medium.

Figure 1B:
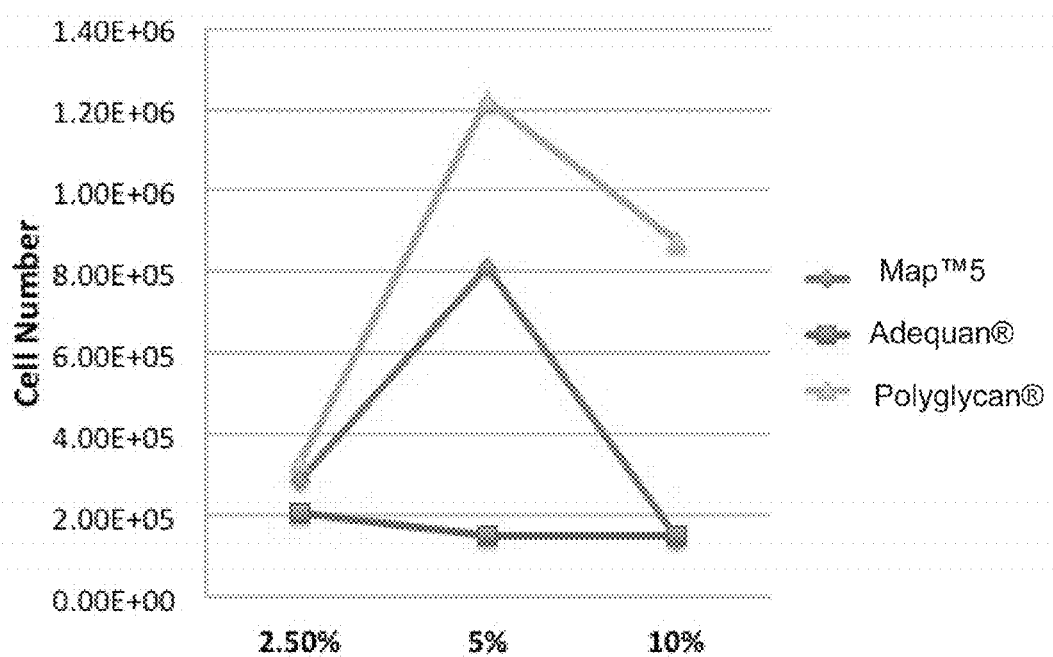

Results:

FIGS. 1A and 1B show the effect of GAG concentration on proliferation on Ad-MSCs was demonstrated in FIGS. 1A-B. Fresh canine adipose SVF cells were plated at equal nucleated cell density and grown for 7 days in culture on tissue culture plastic in the presence of complete growth media (α-MEM containing 20% (v/v) FBS) and the respective concentrations (v/v) of GAG formulations (FIG. 1A). Media was changed at days 3 and 6. Nucleated cell counts were performed by Syto13 staining followed by hemacytometer counting under fluorescence microscopy (FIG. 1B).

Figure 2:
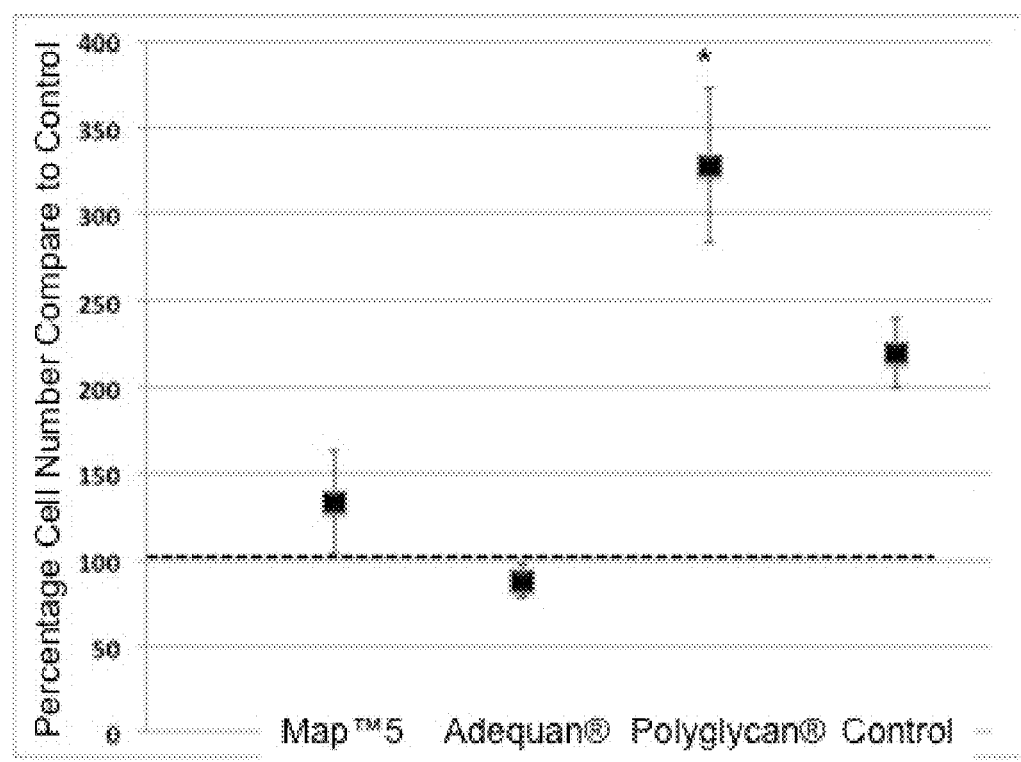
FIG. 2 shows that Ad-MSCs proliferate faster in POLYGLYCAN formulation at 5% concentration (v/v). Fresh canine adipose-derived stromal cells were plated at equal nucleated cell density and grown for 7 days in culture on plastic tissue culture surface in the presence of complete growth media and the respective concentrations (v/v) of GAG formulation. Nucleated cell counts were performed by Syto13 staining followed by hemacytometer counting under fluorescence microscopy *P<0.05.

The invention demonstrates that Ad-MSCs proliferate faster in POLYGLYCAN formulation at 5% concentration (v/v) (see FIG. 2). Fresh canine adipose SVF cells were plated at equal nucleated cell density and grown for 7 days in culture on tissue culture plastic in the presence of complete growth media and the respective concentrations (v/v) of GAG formulation. Nucleated cell counts were performed by Syto13 staining followed by hemacytometer counting under fluorescence microscopy. Data represent average+/−SD for triplicate determinations of cell number at day 7 *$P<0.05$.

Figure 3A:
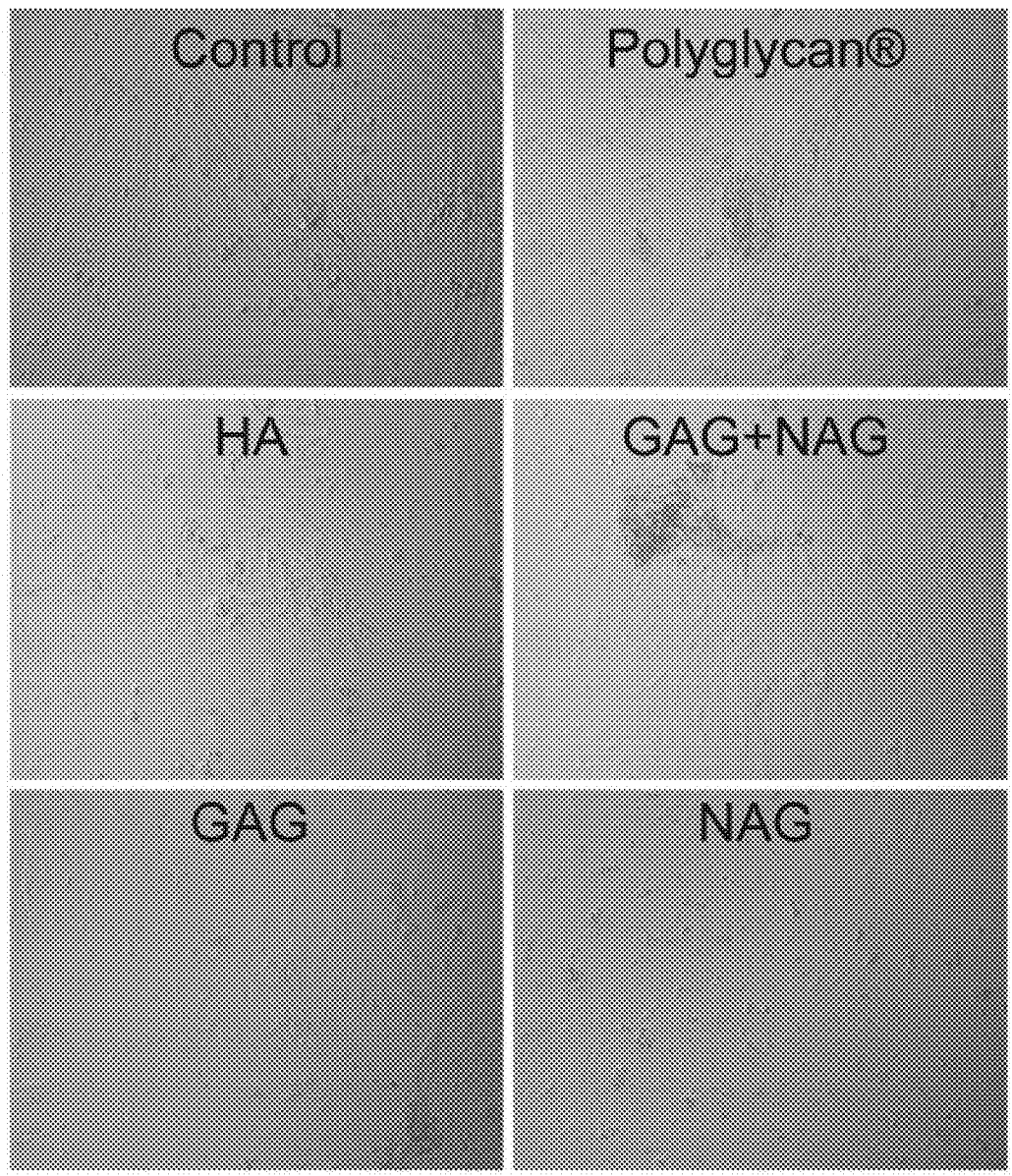
FIGS. 3A and 3B show that Ad-MSCs proliferate faster and express higher levels of Sox2 when cultured in GAG formulations. Canine Ad-MSCs were grown for 6 days in culture in the presence of complete growth media and the respective 5% (v/v) GAG formulation. Magnification=100×. Sox2 levels, a marker of stem cell proliferation, were measured in total RNA samples and normalized to β-Actin.
Figure 3B:
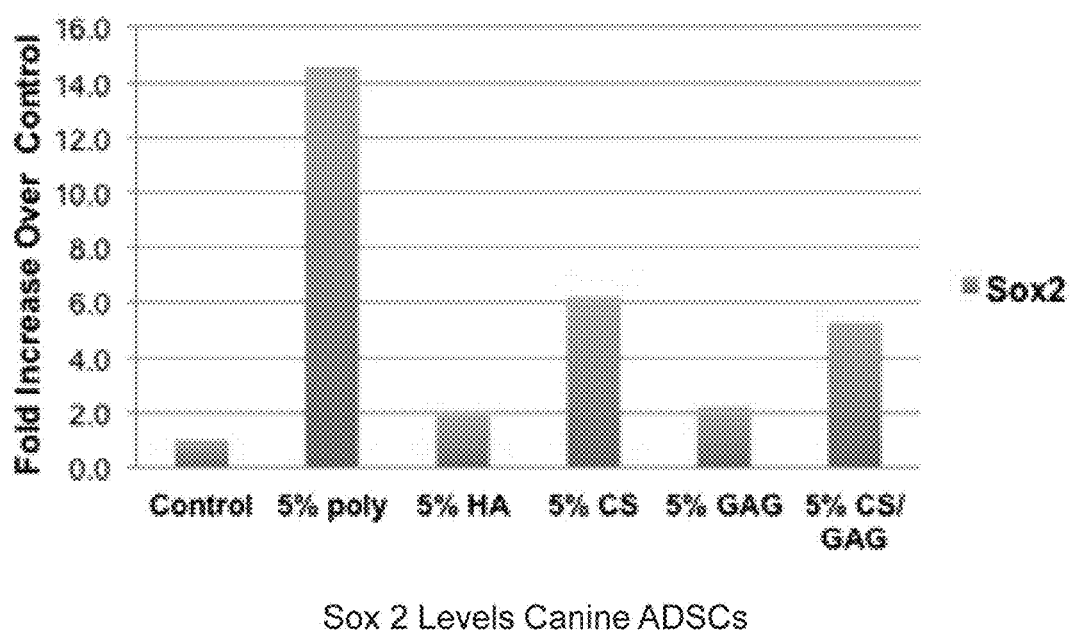

The invention further demonstrates that Ad-MSCs proliferate faster and express higher levels of Sox2 when cultured in GAG formulations (see FIGS. 3A and 3B). Canine Ad-MSCs were grown for 6 days in culture in the presence of complete growth media and the respective 5% (v/v) GAG formulations. Magnification=100×. Sox2 levels, a marker of stem cell proliferation, were measured in total RNA samples and normalized to β-Actin mRNA. Here "GAG" represents poly-sulfated glycosaminoglycan (ADEQUAN). FIG. 3B clearly shows the combination of HA, CS and NaDg in POLYGLYCAN resulted in a substantially greater increase in Sox2 levels.

Figure 4A:
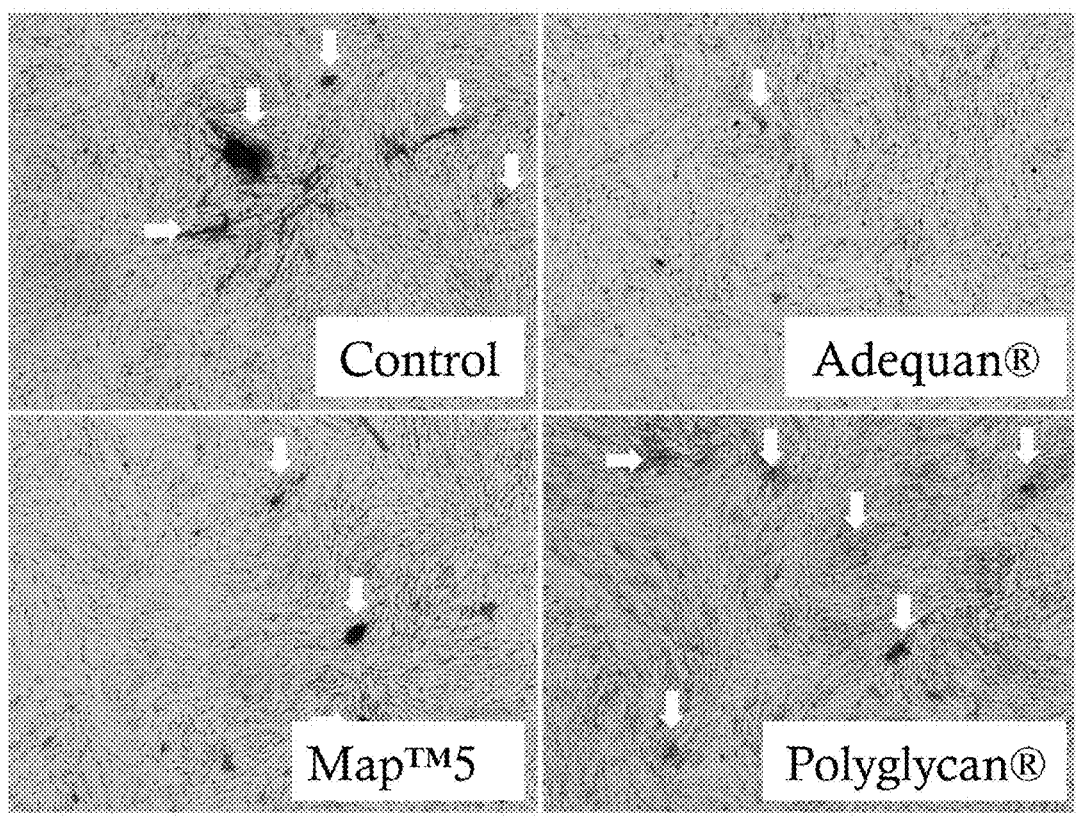
FIGS. 4A and 4B show that colony formation is enhanced by POLYGLYCAN. A total of $0.25 \times 10^{\wedge}6$ nucleated canine adipose SVF cells were plated and grown for 14 days in culture on tissue culture plastic surface. Results shown depict colony formation in Growth Media with 5% (v/v) GAG formulation, *P<0.05.
Figure 4B:
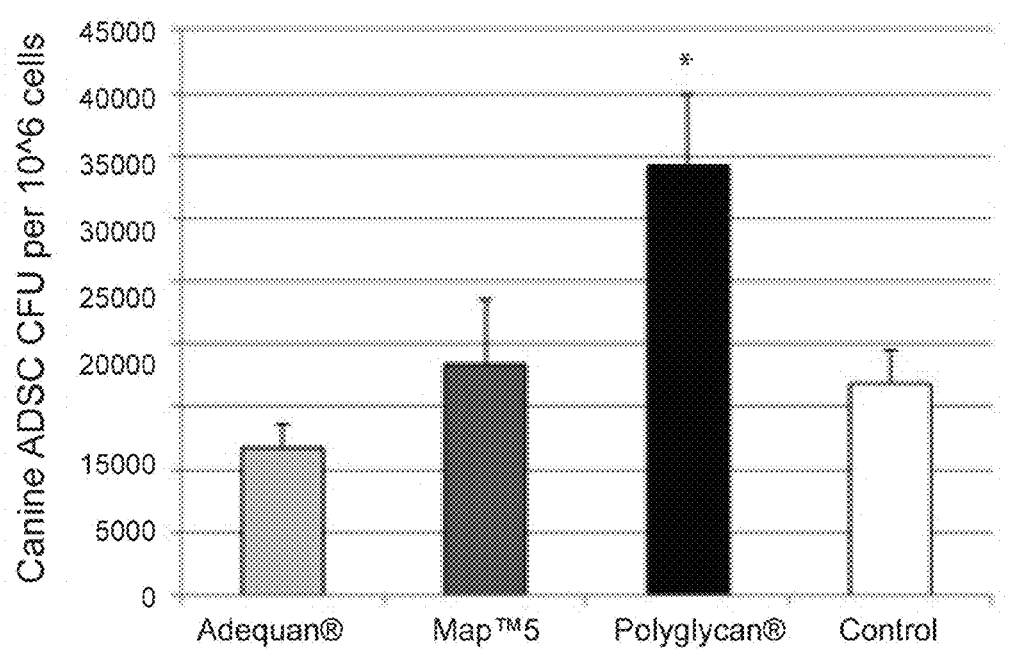

Colony formation is also significantly enhanced by the GAG composition of POLYGLYCAN (see FIGS. 4A, 4B) over poly-sulfated GAG (ADEQUAN) or hyaluronan (MAPS) alone. A total of $0.25\times10^6$ nucleated canine adipose-SVF cells were grown for 14 days in culture on tissue culture plastic. Results shown depict colony formation in Growth Media with 5% (v/v) GAG formulation, *$P<0.05$.

Figure 5:
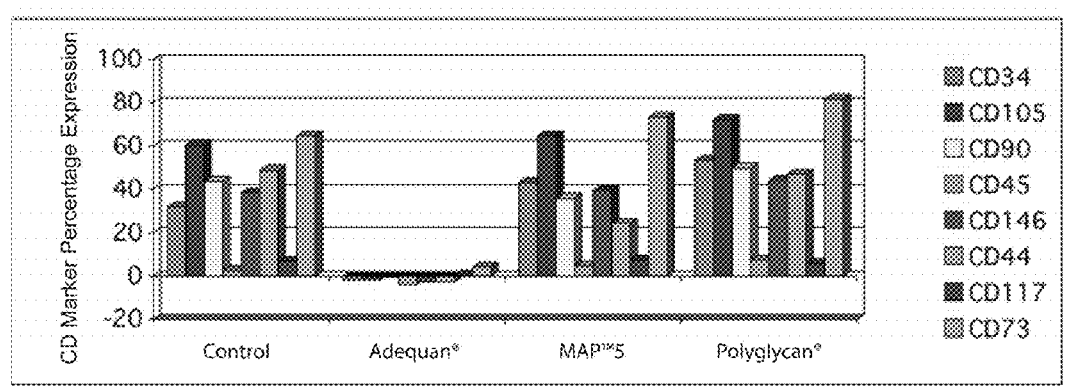
FIG. 5 shows Ad-MSC cell surface marker expression after exposure to HA formulations in vitro for six days. Human Ad-MSC CD marker profiling after 6 days culture in GAG formulation. FACS analysis was performed using the GALLIOS™ Flow Cytometer.

FIG. 5 describes Ad-MSC cell surface marker expression after exposure to GAG formulations in vitro for six days. Human Ad-MSC CD marker profiling after 6 days culture in GAG formulation. FACS analysis done in GALLIOS™ Flow Cytometer.

Figure 6:
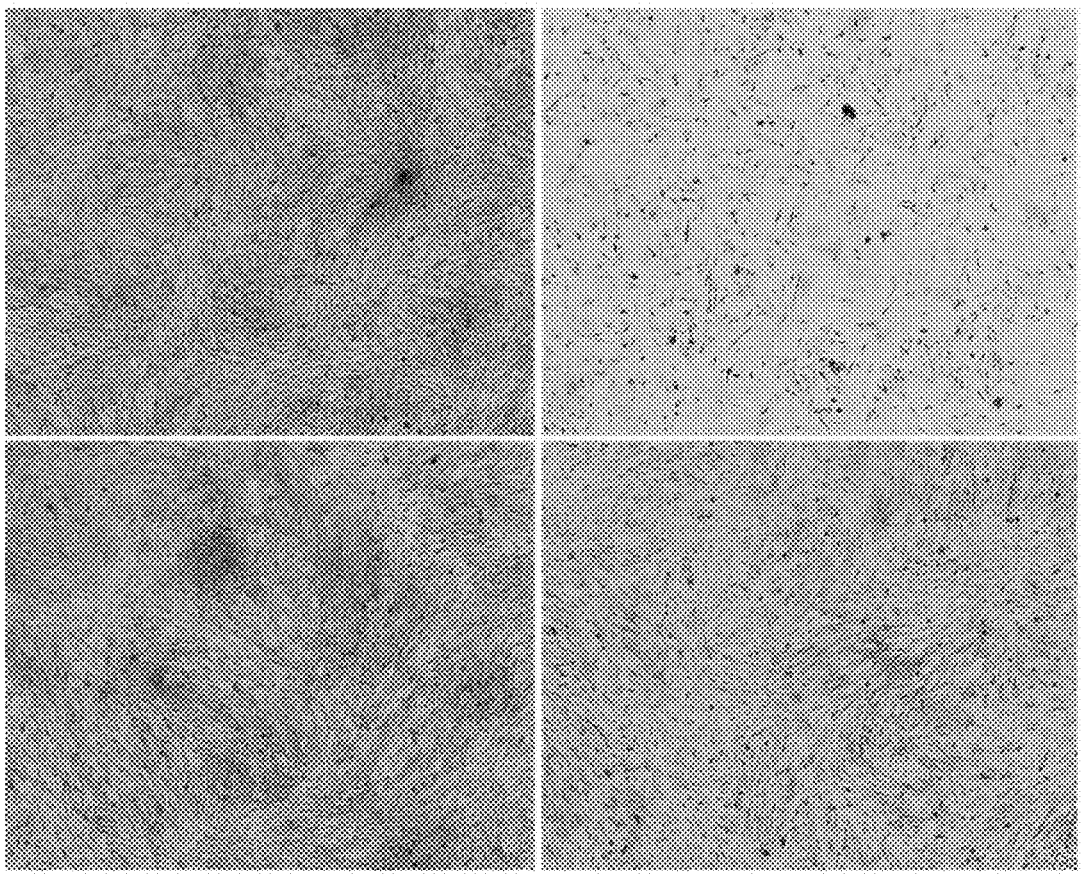
FIG. 6 shows that Ad-MSC proliferation is maintained while osteogenic differentiation is inhibited by GAG formulations containing sulfated GAG in vitro. Cultures were maintained in osteogenic differentiation induction medium for 14 days, in 5% (v/v) formulation. Cultures were fixed with 4% formalin and stained with Alzarin red that stains calcium.

FIG. 6 describes that Ad-MSC proliferation is maintained while osteogenic differentiation is inhibited by GAG formulations containing sulfated GAG in vitro (ADEQUAN and POLYGLYCAN). Cultures were maintained in osteogenic differentiation induction medium for 14 days, in 5% (v/v) formulation. Cultures were fixed with 4% formalin and stained with Alzarin red that stains calcium.

Figure 7:
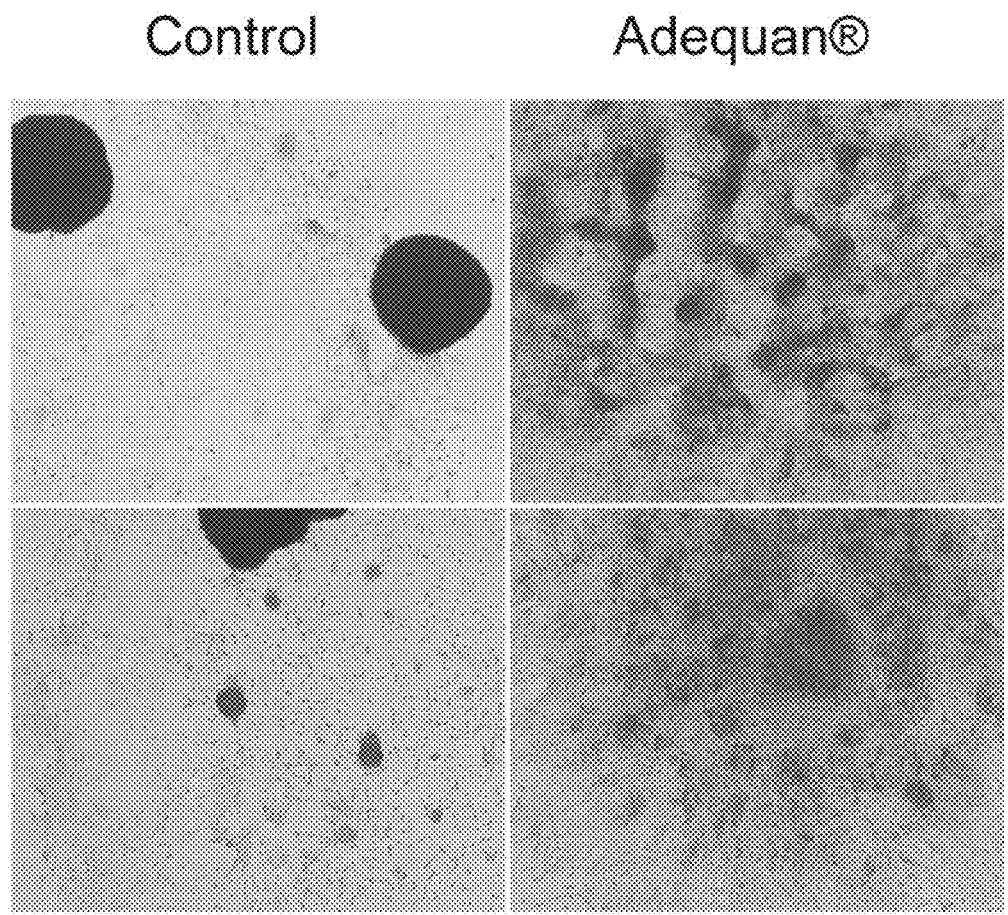
FIG. 7 shows that Ad-MSC proliferation is maintained while chondrogenic differentiation is inhibited by GAG formulations containing sulfated GAG in vitro. Cultures were maintained in chondrogenic differentiation induction medium for 14 days, in 5% (v/v) formulation. Cultures were fixed with 4% formalin and stained with Alcian Blue that contains chondrocytes.

FIG. 7 describes that Ad-MSC proliferation is maintained while chondrogenic differentiation is inhibited by GAG formulations containing sulfated GAG in vitro (ADEQUAN and POLYGLYCAN). Cultures were maintained in chondrogenic differentiation induction medium for 14 days, in 5% (v/v) formulation. Cultures were fixed with 4% formalin and stained with Alcian Blue that contains chondrocytes.

Figure 8:
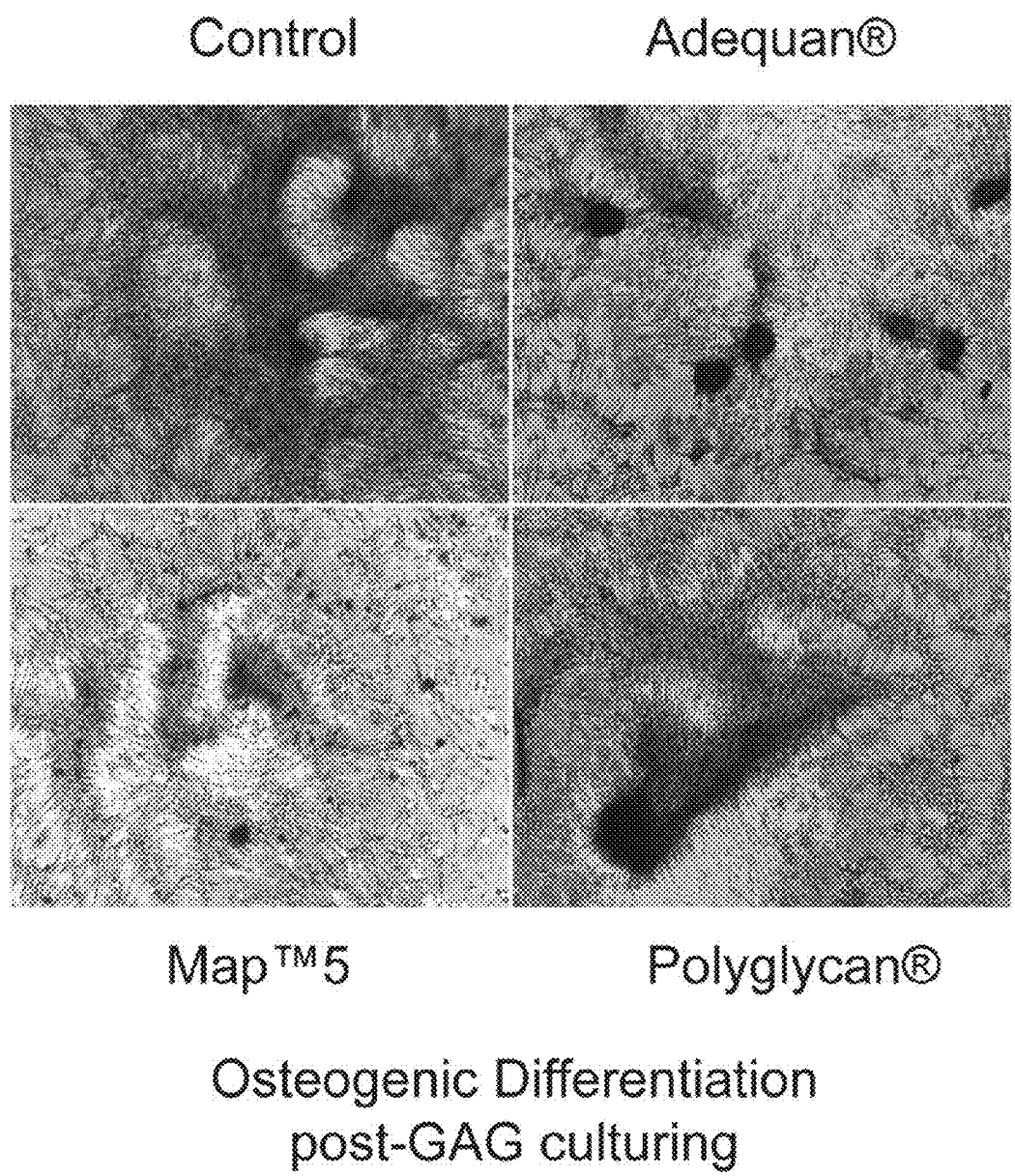
FIG. 8 shows that osteogenic differentiation is highly efficient in Ad-MSC after in vitro exposure and later removal of GAG-containing formulations. Cultures were maintained in osteogenic differentiation medium for 14 days after being cultured in GAG formulation for 6 days. Cultures were fixed with 4% formalin and stained with Alzarin red that stains calcium.

FIG. 8 describes that osteogenic differentiation is highly efficient in Ad-MSC after in vitro exposure and later removal of GAG-containing formulations. Cultures were maintained in osteogenic differentiation medium for 14 days after being cultured in GAG formulation for 6 days. Cultures were fixed with 4% formalin and stained with Alzarin red that stains calcium.

Figure 9:
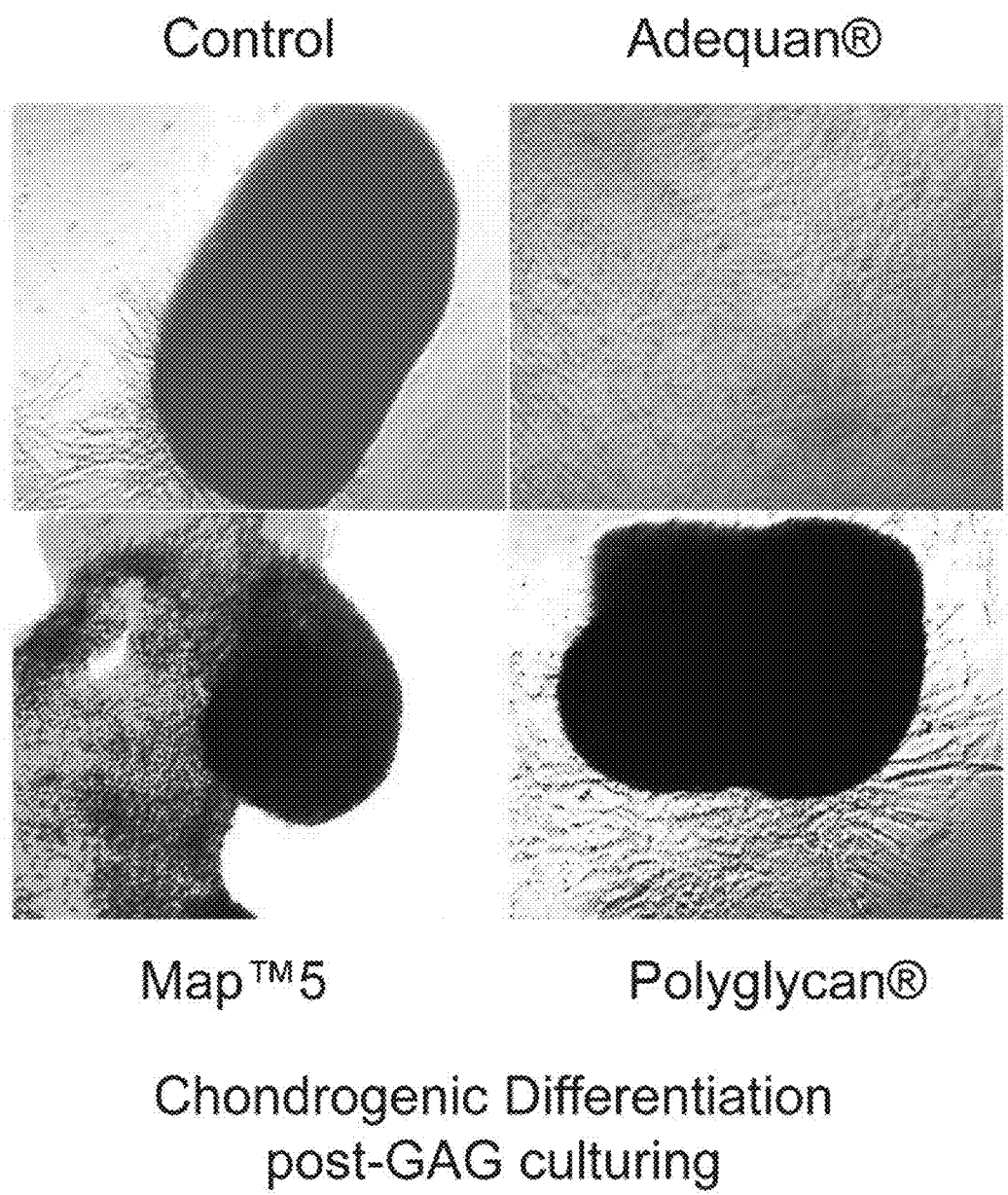
FIG. 9 shows that chondrogenic differentiation is highly efficient in Ad-MSC after in vitro exposure and later removal of HA-containing formulations. Cultures were maintained in chondrogenic differentiation induction medium for 14 days after being cultured in GAG formulation for 6 days. Cultures were fixed with 4% formalin and stained with Alcian Blue.

FIG. 9 describes that chondrogenic differentiation is highly efficient in Ad-MSC after in vitro exposure and later removal of HA-containing formulations. Cultures were maintained in chondrogenic differentiation induction medium for 14 days after being cultured in GAG formulation for 6 days. Cultures were fixed with 4% formalin and stained with Alcian Blue.

Figures 10, 11:
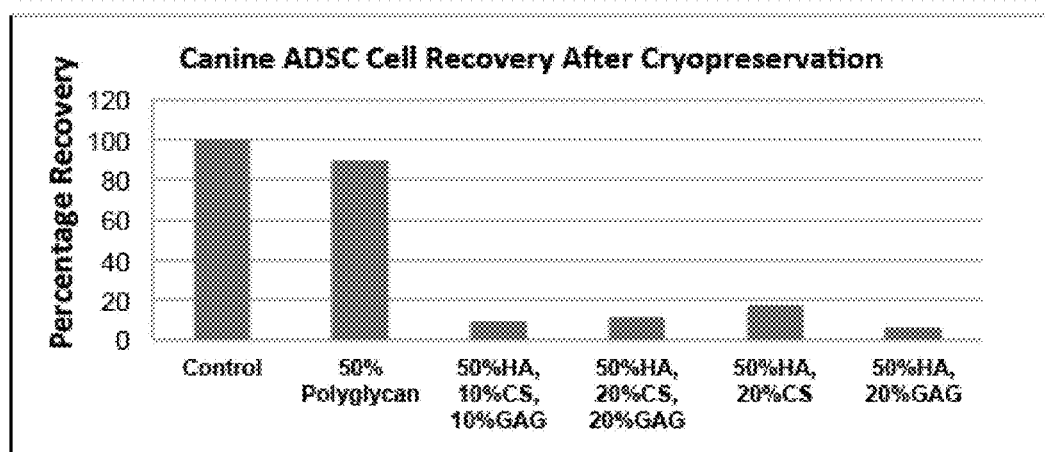
FIG. 10 shows cell counts of nucleated viable canine stromal vascular cells after cryopreservation in the presence of GAG-containing formulations compared to cells cryopreserved in 5% DMSO and 85% fetal bovine serum (FBS).
FIG. 11 shows flow activated cell sorting (FACS) analysis of cell surface marker expression of canine stromal vascular cells after cryopreservation in the presence of GAG-containing formulations compared to cells cryopreserved in 5% DMSO and 85% fetal bovine serum (FBS).

FIG. 10 shows recovery of nucleated, viable canine adipose SVF after cryopreservation in the presence of GAG-containing formulations compared to cells cryopreserved in control media (5% DMSO, 10% α-MEM, 85% fetal bovine serum (FBS)). Cryopreservation in 50% POLYGLYCAN resulted in significantly higher ADSC recovery than any other GAG combination. $5.5 \times 10^6$ fresh canine stromal vascular cells were aliquotted in duplicate to 15 ml sterile conical tubes for each condition and concentrated to a pellet by centrifugation at 600×g for 10 minutes. Supernatants were removed by aspiration, and pellets were resuspended in 1.5 control or test cryopreservation media and transferred to individual 2.0 ml sterile cryovials. Cryovials were then cooled to −80 C in a Mr. Frosty freezing container (Nalgene, Rochester, N.Y.). After freezing, cryovials were maintained at −80 C for 20 days. Cryopreserved cells were rapidly thawed in a 37 C water bath. Total cell count was determined with the aid of Syto 13 nuclear stain and nonviable cell count was determined with the aid of Trypan blue dye. Percent viability was immediately determined as ((total cells−nonviable cells/total cells)×100).

FIG. 11 shows Flow Cytometry analysis of cell surface marker expression by human adipose SVF cells after cryopreservation in the presence of POLYGLYCAN (PO) GAG-containing formulations (5-50% (v/v)) compared to cells cryopreserved in control media (5% DMSO, 10% α-MEM, 85% fetal bovine serum (FBS)). Cryopreservation was performed as described for FIG. 10. After storage at −80 C for 14 days, cells were thawed and placed in culture for 24 h in 75 cm² plastic tissue culture dishes with media (α-MEM containing 20% (v/v) FBS). Surface marker expression for CD34, CD44, CD45, CD73, CD90, CD105, and CD117 was assessed on plastic adherent cells by Flow Cytometery using a GALLIOS™ Flow Cytometer (Beckman Coulter, Brea, Calif.) and compared to cells from the same sample cultured for 24 h under the same conditions but not cryopreserved.

Figure 12:
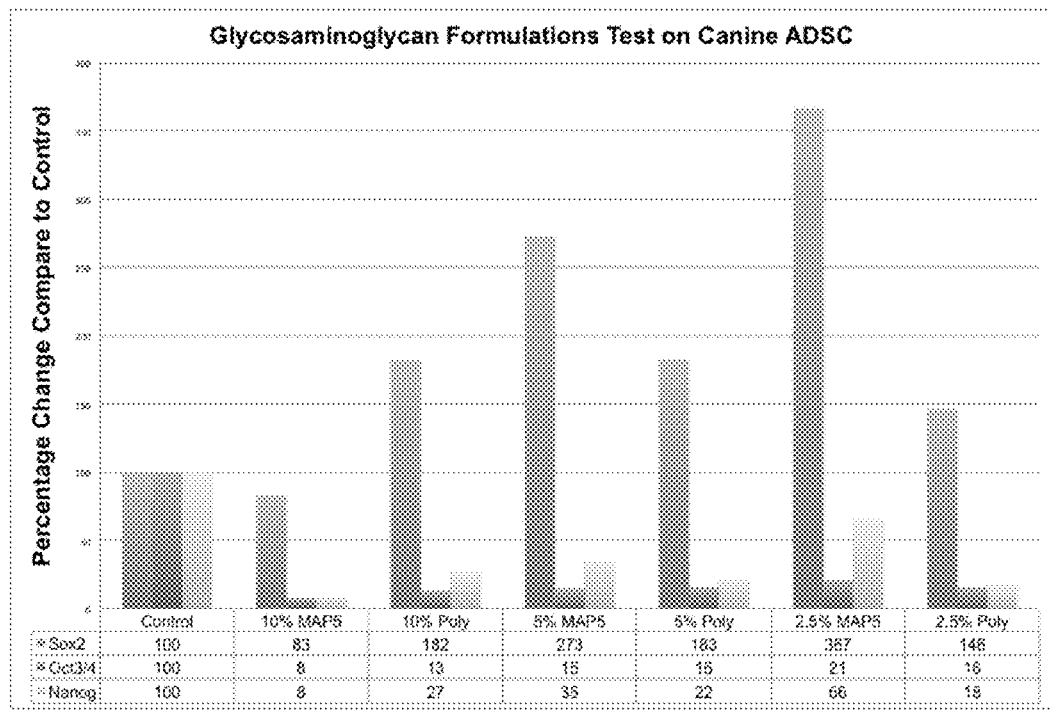
FIG. 12 shows expression of stem cell markers in Canine Ad-MSC growing in GAG formulations.

FIG. 12 shows changes in gene expression in canine Ad-MSC after culturing in media containing GAG formulation for 6 days. Fresh canine adipose SVF cells were plated at a density of $5 \times 10^5$ cells per well in 6 well plates and cultured for 6 days on tissue culture plastic in α-MEM containing 20% (v/v) FBS and GAG formulations ranging from 2.5-10% (v/v). Media was changed at day 3. At day 6 total RNA was prepared and gene expression for selected genes was determined by quantitative rt-PCR.

Figure 13:
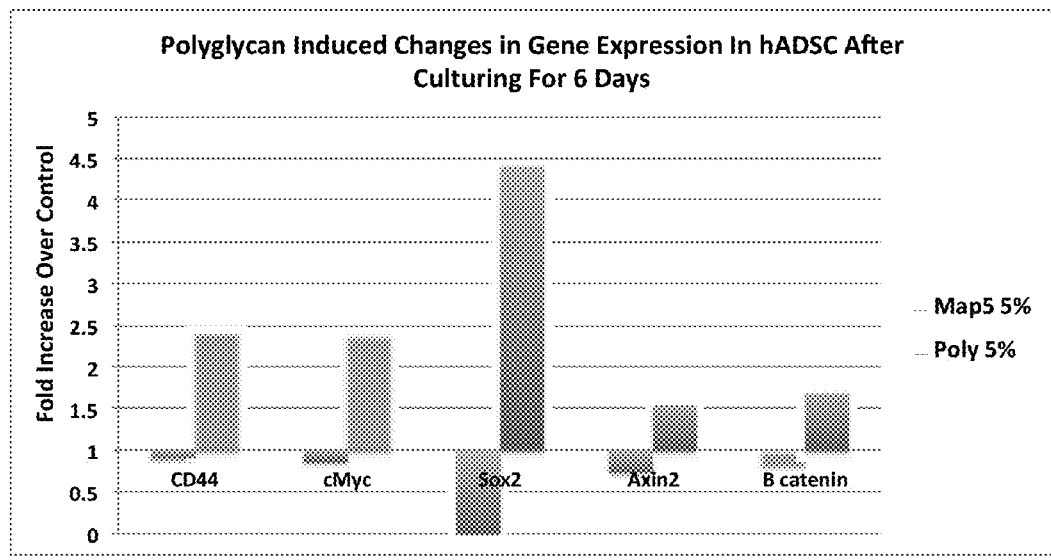
FIG. 13 shows POLYGLYCAN induced changes in gene expression in hADSC after culturing for 6 days.

FIG. 13 shows changes in gene expression in human Ad-MSC after culturing in media containing GAG formulation for 6 days. Fresh human adipose SVF cells were plated at a density of $7.5 \times 10^5$ cells per well in 6 well plates and cultured for 6 days on tissue culture plastic in control media (α-MEM containing 20% (v/v) FBS) or control media supplemented with 5% (v/v) POLYGLYCAN or MAPS media was changed at day 3. At day 6 total RNA was prepared and gene expression for selected genes was determined by quantitative rt-PCR. Bars depict relative changes in gene expression for cells cultured in media containing GAG formulation to cells cultured in control media.

Figure 14:
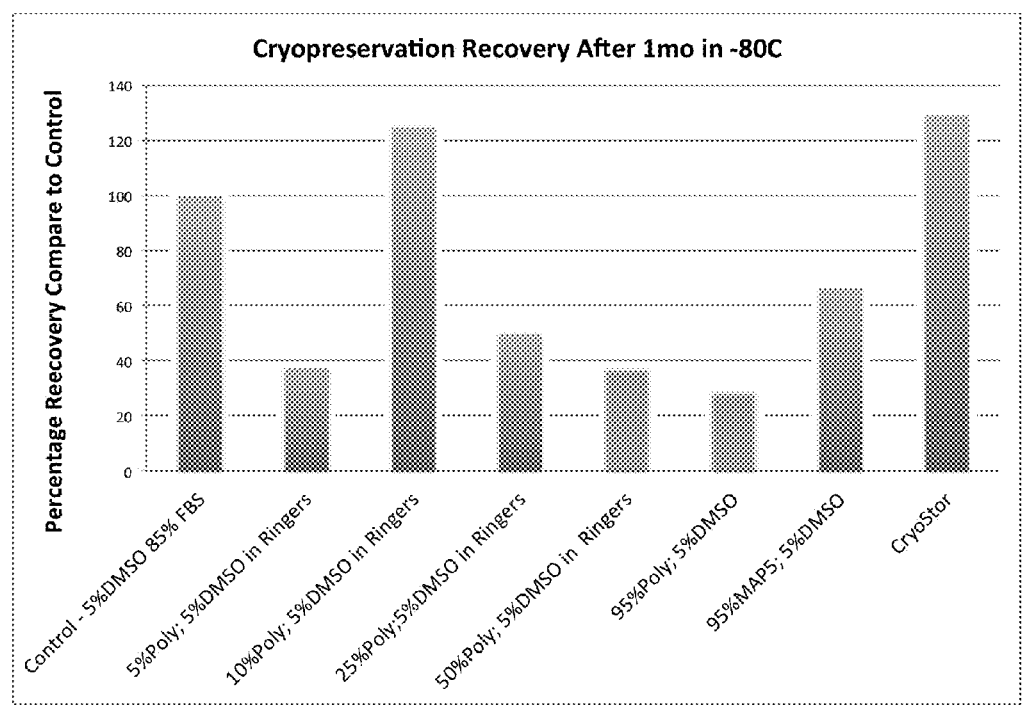
FIG. 14 shows cryopreservation recovery after 1 month in −80° C.

FIG. 14 shows recovery of nucleated, viable canine stromal vascular cells after cryopreservation in the presence of POLYGLYCAN GAG-containing formulations compared to cells cryopreserved in control media (5% DMSO, 10% α-MEM, 85% fetal bovine serum (FBS)) or commercial cryopreservation media (CRYOSTOR, BioLife Solutions, Inc., Bothell, Wash.). $5.5 \times 10^6$ fresh canine adipose SVF cells were aliquotted in duplicate to 15 ml sterile conical tubes for each condition and concentrated to a pellet by centrifugation at 600×g for 10 minutes. Supernatants were removed by aspiration, and pellets were resuspended in 1.5 control or test cryopreservation media and transferred to individual 2.0 ml sterile cryovials. Cryovials were then cooled to −80 C in a Mr. Frosty freezing container (Nalgene, Rochester, N.Y.). After freezing, cryovials were maintained at −80 C for 20 days. Cryopreserved cells were rapidly thawed in a 37 C water bath. Total cell count was determined with the aid of Syto 13 nuclear stain and nonviable cell count was determined with the aid of Trypan blue dye. Percent viability was immediately determined as ((total cells−nonviable cells/total cells)×100).

Figure 15:
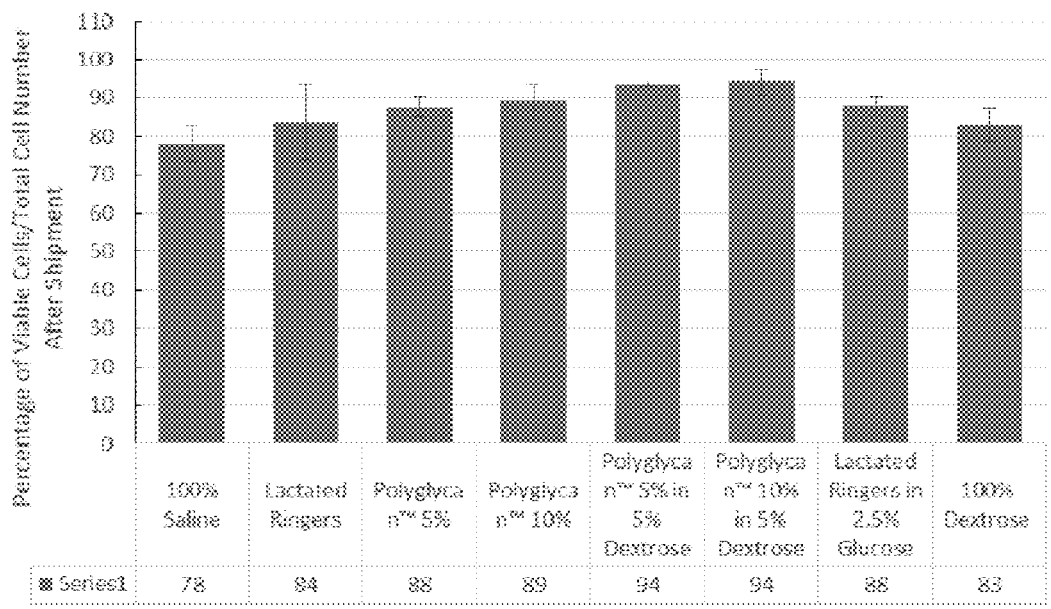
FIG. 15 shows cultured hADSC stability analysis after shipment.

FIG. 15 shows the effect of storage solution composition on viability of cultured hAd-MSC subjected to overnight shipment. $1.5 \times 10^6$ viable human Ad-MSC were suspended in 1.0 ml test solution and transferred to sterile cryovials. Cryovials were placed into a styrofoam shipping container with a cold pack to maintain temperature at 2-8 C. The shipping container was sealed, transported to a local shipping center, and shipped by overnight courier to the laboratory location. 24 h after placement of cryovials in the container, the container was opened to recover cells from cryovials and assess cell viability as described for FIG. 10. Bars depict the mean of triplicate determinations for each test solution.

Figure 16:
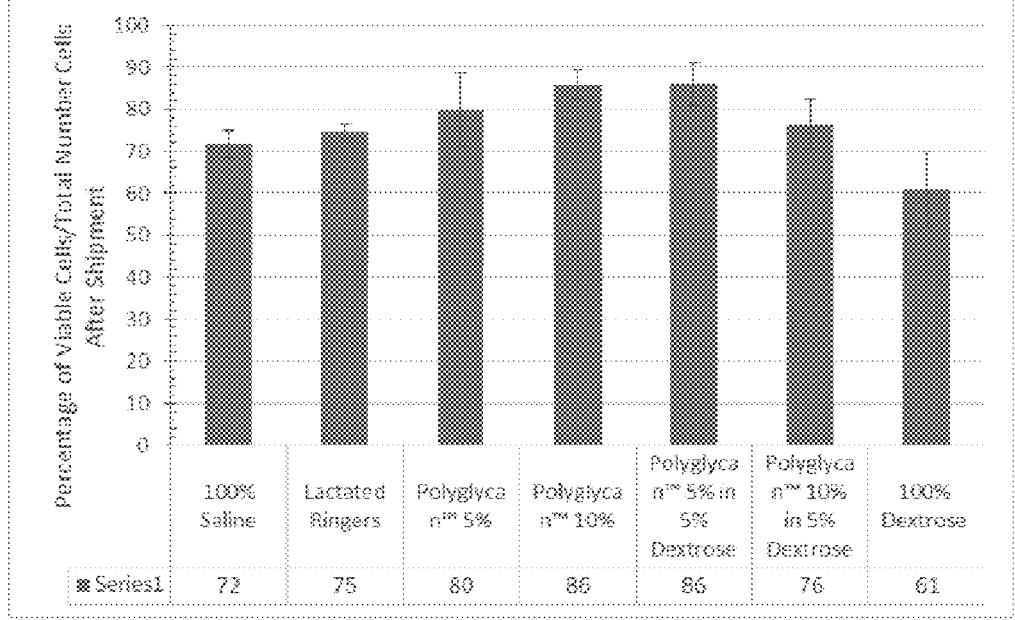
FIG. 16 shows fresh hADSC stability analysis after shipment.

FIG. 16 shows the effect of storage solution compositions on viability of fresh adipose SVF cells subjected to overnight shipment. Immediately after isolation from human lipoaspirate $1.5 \times 10^6$ viable human stromal vascular cells were suspended in 1.0 ml test solution and transferred to sterile cryovials. Cryovials were placed into a styrofoam shipping container with a cold pack to maintain temperature at 2-8 C. The shipping container was sealed, transported to a local shipping center, and shipped by overnight courier to the laboratory location. 24 h after placement of cryovials in the container the container was opened to recover cells from cryovials and assess cell viability as described for FIG. 10. Bars depict the mean of triplicate determinations for each test solution.

In view of the studies and results provided above, regenerative cells exposed to low concentrations of GAG formulations of the invention such as a POLYGLYCAN composition increase cell proliferation and colony forming potential (P<0.05), and enrich the proportion of cultured cells expressing key regenerative cell markers such as CD44, CD90, CD146, CD117, CD73, and CD105. In addition, these formulations significantly increased Sox2 levels, (a marker of a cell's stemness or potency) (P<0.05), and influence cellular pathways such as the Wnt pathways, which are known to be key in the regulation of regenerative cell proliferation. Noted effects were markedly dose dependent. The presence of these GAGs in vitro promoted proliferation and self-renewal, even in the presence of differentiation cues in the culture media. These effects were reversible as efficient differentiation was observed in the absence of GAG formulations.

In view of the effects of POLYGLYCAN on gene expression in cultured canine Ad-MSC, the data indicate a significant increase in CD44 levels (receptor for hyaluronic acid (HA)), a decrease in the level of differentiation markers, a significant decrease in the levels of apoptosis related genes, a significant decrease in expression of inflammatory cytokines such as IL1b and IL6, an increase in the level of Col. 1A, and increase in the levels of (FGFs) growth factor.

Thus, the Examples provided above demonstrate that effects of GAG formulations were strongly dose-dependent, and profound differences were observed between GAG formulations. A combination of hyaluronic acid, chondroitin sulfate, and glucosamine in POLYGLYCAN composition at dilutions of 1-10% (v/v) in growth media was found to be optimal for promoting proliferation and self-renewal. Addition of HA alone to culture media elicited qualitatively similar, but of lesser magnitude effects on the marker of sternness, Sox2, correlated with effects on cell proliferation. Removal of HA containing formulations enabled lineage specific differentiation in appropriate culture media. In contrast, addition of the commercial GAG formulation ADEQUAN (only poly-sulfated GAG) inhibited proliferation and dramatically reduced chondrogenic potential of regenerative cells. These results indicate that an optimal GAG formulation for culturing and administration of stem and regenerative cells is based on GAG ratios in the POLYGLYCAN composition.

The use of the GAG formulation for preservation, shipping, cryopreservation, or suspension is also evidenced at the GAG dilutions described herein. The invention provides that MSCs proliferate more rapidly in culture media supplemented with a formulation containing POLYGLYCAN at 5% (v/v), and MSCs are capable of efficient differentiation in vitro once GAG formulation is removed. POLYGLYCAN at low concentration (e.g., 5%) in culture media induces expression of markers of MSCs. The commercial GAG formulation MAPS containing only HA appears to be pro-mitotic, but less potent than POLYGLYCAN. Further, cryopreservation media containing 10% POLYGLYCAN, 5% DMSO, 85% Ringer's yield performs at least as well as standard control media containing FBS and DMSO.

The invention claimed is:

1. A method of culturing cells having multi-lineage differentiation potential, comprising culturing the cells for at least 24 hours in a cell culture media comprising a glycosaminoglycan (GAG) composition, wherein said GAG composition comprises hyaluronic acid, chondroitin sulfate and N-acetyl D-glucosamine in a relative weight ratio of 1:20:20, wherein said GAG composition is at a concentration of 5-10% (v/v), and wherein the cultured cells have an enhanced in vitro expansion rate and maintain multi-lineage differentiation potential compared to cells having a multi-lineage differentiation potential not cultured in the media.

2. The method of claim 1, wherein said composition is at a concentration of 5-7% (v/v).

3. The method of claim 2, wherein said composition is at a concentration of 5% (v/v).

4. The method of claim 1, wherein said GAG composition comprises hyaluronic acid, CS4 and CS6 chondroitin sulfate and N-acetyl D-glucosamine at a concentration 5-10% (v/v).

5. The method of claim 1, wherein said cells are treated with a media supplement comprising the GAG composition and then culturing the cells.

6. The method of claim 1, wherein said cells are grown on a surface coated with a soluble matrix comprising the GAG composition.

7. The method of claim 1, wherein said cell is an adipose-derived mesenchymal stem cell (Ad-MSC).

8. The method of claim 1, wherein the cells are cultured for at least 3 days.

9. The method of claim 1, wherein the cells are cultured for at least 6 days.

10. The method of claim 1, wherein the GAG composition comprises about 5 mg/ml hyaluronic acid sodium salt, about 100 mg/ml sodium chondroitin sulfate, and about 100 mg/ml N-acetyl D-glucosamine.

* * * * *